United States Patent [19]
Chang et al.

[11] Patent Number: 5,674,284
[45] Date of Patent: Oct. 7, 1997

[54] INTRAOCULAR LENS WITH FRACTURE RESISTANT HAPTICS

[75] Inventors: Shiao H. Chang, Arcadia; Charles H. Sherwood, Upland; Bruce A. Tunberg, Pomona; Paul D. Rice, Chino; Walker L. Gordy, Victorville, all of Calif.

[73] Assignee: Iolab Corporation, Claremont, Calif.

[21] Appl. No.: 605,454

[22] Filed: Feb. 26, 1996

Related U.S. Application Data

[63] Continuation of Ser. No. 387,971, Feb. 10, 1995, abandoned, which is a continuation of Ser. No. 98,693, Jul. 28, 1993, abandoned.

[51] Int. Cl.⁶ ........................................... A61F 2/16
[52] U.S. Cl. ........................................... 623/6; 264/1.7
[58] Field of Search .................................. 264/1.7; 623/6

[56] References Cited

U.S. PATENT DOCUMENTS

| | | | |
|---|---|---|---|
| 4,687,485 | 8/1987 | Lim et al. | 623/6 |
| 4,995,879 | 2/1991 | Dougherty | 623/6 |
| 5,037,435 | 8/1991 | Chang et al. | 264/1.7 X |
| 5,169,569 | 12/1992 | Ingram et al. | 264/2.7 |
| 5,182,053 | 1/1993 | Creasman et al. | 264/1.7 X |
| 5,322,649 | 6/1994 | Rheinish et al. | 264/1.7 X |

FOREIGN PATENT DOCUMENTS

0438043A2  7/1991  European Pat. Off.

*Primary Examiner*—Mary Beth Jones
*Attorney, Agent, or Firm*—Loeb & Loeb LLP

[57] ABSTRACT

The polymethyl methacrylate (PMMA) or copolymer thereof used to produce one-piece intraocular lenses is modified by a compression molding process to produce a much tougher material with improved mechanical properties. The process takes material in rod form and compresses into lens blanks. The molded lens blanks receive little or no compression strain in the center 4 mm optic zone. The compression is limited to the periphery region outside the center 4 mm zone. The intraocular lens fabricated from the molded lens blank exhibits greatly increased haptic mechanical properties and resistance to breakage.

9 Claims, 4 Drawing Sheets

INTRAOCULAR LENS WITH FRACTURE RESISTANT HAPTICS

This is a continuation of application Ser. No. 08/387,971 filed on Feb. 10, 1995, now abandoned, which in turn is a continuation of application Ser. No. 08/098,693 filed Jul. 28, 1993, now abandoned.

BACKGROUND OF THE INVENTION

This invention relates to an improved intraocular lens for implantation in the eye following removal of the natural lens during cataract surgery. More specifically, it relates to a compression molding process for manufacturing an intraocular lens in which the supporting haptics exhibit an increased resistance to breakage during manipulation.

The filamentary haptic of an intraocular lens is designed to facilitate insertion of the lens into the eye and to provide stable fixation of the implanted lens to prevent the lens from decentering. The filamentary haptic is attached to and extends outwardly from the periphery of the optical lens body. Most intraocular lenses have two haptics displayed at positions 180° apart from each other on the optic lens body.

Intraocular lenses are typically of two types: the three-piece lens where two haptics are mechanically fixed to the lens optic, and the one-piece lens where the haptics and optic are made as a single unit.

It is critical that the haptic of the lens exhibits significant resistance to breakage during use. Although certain haptic materials such as polypropylene used in construction of a three-piece lens offer acceptable resistance to breakage, other conventionally used haptic materials such as polymethyl methacrylate (PMMA) are brittle and frequently prone to breakage. This problem becomes especially acute when the haptics are lathe cut from a single lens blank to prepare a one-piece lens with integrally attached haptics. The problem of haptic breakage is a serious one, and efforts have been made to provide the haptics with an increased resistance to breakage.

Several thermoplastic forming techniques have been used to induce orientation in the material to impart enhanced mechanical properties in PMMA intraocular lens haptics. One such effort is disclosed in U.S. Pat. No. 5,169,569. This patent describes preparing intraocular lenses with haptics exhibiting greater ductility and fatigue resistance. The PMMA sheet plastic is modified by means of blowing the sheet into a hemispherical bubble followed by forming into a flattened circular portion.

A second effort is disclosed in European Patent Application 0 438 043 A2. The PMMA material is modified by multi-axis stretching to produce haptics with increased tensile strength, flexibility and resiliency.

Another previous method of making intraocular lenses was through a compression molding process which introduced deformation, and thus material orientation, throughout the entire lens. This type of lens demonstrated enhanced haptic mechanical property performance against breakage, but the particular method shows a less desirable Nd:YAG laser interaction characteristic.

The Nd:YAG laser is used for treatment of posterior capsular opacification. In this treatment the posterior capsule is ruptured after being hit with a focused laser beam. The rupture typically leaves a hole 2 mm–4 mm in diameter through which light can pass. Posterior capsular opacification usually occurs several months after intraocular lens implantation. During the laser procedure, the intraocular lens is frequently hit by the beam. This hit, depending upon the energy of the burst and the location of the hit, can cause varying degrees of damage to the lens. It has been shown in our work that the laser energy interacts differently with oriented and nonoriented materials. In the nonoriented material, referred to as conventional material, the laser energy is dissipated along the three axes of the lens. This typically results in distinct cracks which may propagate a significant distance through the thickness dimension of the lens. The oriented material typically retards crack propagation through the thickness dimension and therefore demonstrates more extensive lateral cracking.

While this is not a vision compromising condition, it is undesirable because it results in light scattering from oblique illumination making eye examinations considerably more difficult. The optic material described in this invention is oriented, but the degree of orientation is balanced such that the resulting crack propagation behavior is similar to the nonoriented material.

A method used to produce a one-piece intraocular lens having a low degree of orientation in the optic region is by injection molding. This previously employed method resulted in an optic region with acceptable characteristics under YAG laser irradiation, but the haptic region was also insufficiently oriented, resulting in an unacceptably high fracture rate.

It is, therefore, an object of the present invention to provide an improved intraocular lens wherein the haptics exhibit enhanced mechanical properties and resistance to breakage while the optics exhibit the conventional Nd:YAG laser interaction characteristics, and a process for making such a lens.

It is a further object of the invention to provide a one-piece PMMA intraocular lens made by the compression molding process and exhibiting the above properties.

SUMMARY OF THE INVENTION

The above objects are achieved by a one-piece intraocular lens having the material of the lens substantially oriented in the haptic region while having the material of the lens substantially non-oriented or of balanced orientation (between the radial, planar dimension and the thickness dimension) in the optic region, and a novel process of heating and compression molding PMMA rod into a lens blank such that little or no compression strain is introduced in the center 4 mm optic zone allowing all of compression to be accomplished in the periphery outside the 4 mm optic zone of a lens blank. This improves the mechanical characteristics of the material in the periphery (haptic region), while retaining the untreated fracture behavior for subsequent YAG laser procedures in the optic (central region). A one-piece intraocular lens is made by machining a single molded lens blank produced as described above to form a central lens body and at least one filamentary haptic integrally attached to and extending outwardly from the periphery of the lens body.

A filamentary haptic of the improved intraocular lens of this invention exhibits surprisingly dramatic resistance to breakage under adverse handling conditions. The process for making this improved lens is straightforward and requires only conventional processing equipment. The resistance to breakage is achieved without the loss of the physical or mechanical integrity of the haptic, or any other property which is necessary for proper functioning and use of the haptic. In addition, the properties of the optic lens body, including and not limited to optical performance and Nd:YAG laser interaction, remain unchanged.

DETAILED DESCRIPTION OF THE INVENTION

Figure 1:
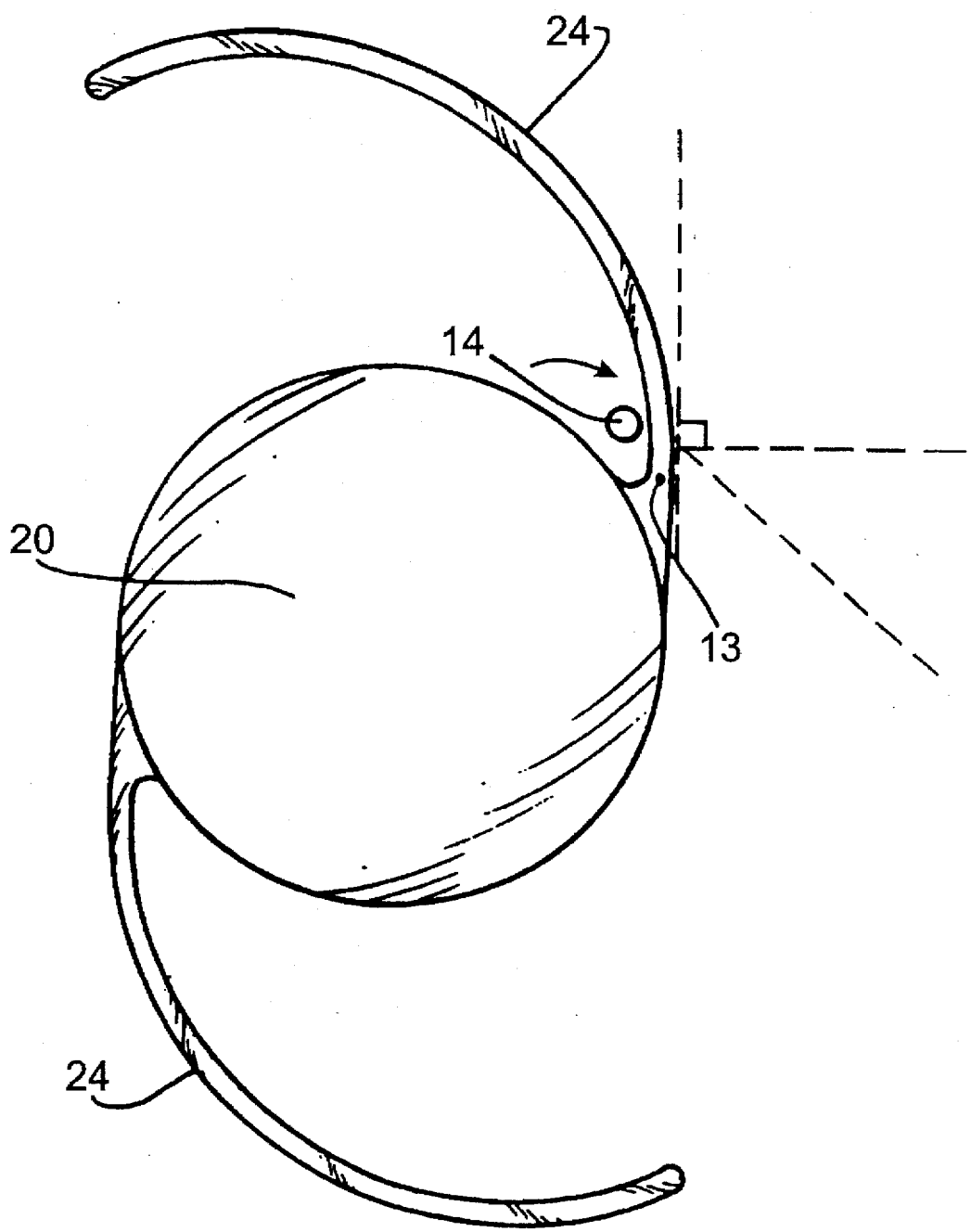
FIG. 1 is a top view of a one-piece intraocular lens embodying principles of the present invention and showing the location and direction of rotation used in brittleness testing.

Many different intraocular lens configurations and sizes may employ the present invention. A typical one-piece intraocular lens configuration 20 is illustrated in FIG. 1, showing an optic or lens body 20 suitably shaped for proper focusing according to methods well-known to those practicing in the field of intraocular lens manufacture, and having integrally formed supporting elements or haptics 24 extending therefrom. The lens 20 may be bi-convex, or plano-convex, concave-convex or any other optical configuration as desired. The optic may also have refractive and diffractive optic portions, several refractive curves or an aspheric surface to give bifocal or multifocal capabilities.

In lenses of this type the central portion or optic is a solid body of about 4 to 7 mm in diameter, with the very small cross section haptics extending outwardly to create an overall size of between about 9 and 14 mm. As is known to those working in the field, any forces exerted on the haptics create high stress at the junction between the haptics and the optic from which the haptics are generally cantilevered. Thus high strength and flexibility are major considerations.

According to principles of the present invention, an intraocular lens of any one of a variety of known haptic configurations and optic sizes is made of a material which enables the lens to provide highly desirable quality of increased strength and flexibility. Instead of being made of a material, such as conventional PMMA which is generally randomly oriented, as occurs in the standard condition of the material, lenses of the present invention are made of PMMA or related materials, as will be more fully described below, that have been processed to provide preferential orientation, resulting in greatly increased resistance to breakage. In general, to obtain these properties, PMMA in short rod form is compression molded to provide different preferential orientations between the center 4 mm optic zone and periphery outside the 4 mm zone of the molded blank to impart enhanced mechanical properties in the periphery zone where the haptics are located.

This is accomplished by introducing little or no compression strain in the center 4 mm optic zone and allowing compression to take place in the periphery region outside the 4 mm zone. Material processed in a similar manner but produced with very different characteristics of orientation in the center 4 mm region has been employed in the manufacture of intraocular lenses.

The present invention presents a great improvement over the previous practice. While the lenses made according to the practice of orienting all the material in the lens blank used to make one-piece intraocular lenses have demonstrated haptic resistance to breakage, the optics exhibit less desirable YAG laser interaction characteristics.

Materials which can be employed to provide enhanced mechanical properties of the intraocular lenses of the present invention include in addition to PMMA: copolymers of PMMA, such as butyl acrylate, ethyl acrylate, and lauryl acrylates. Other suitable polymers characterized as optically clear, thermoplastic polymers compatible with the body alternately may be employed.

Figure 2A:
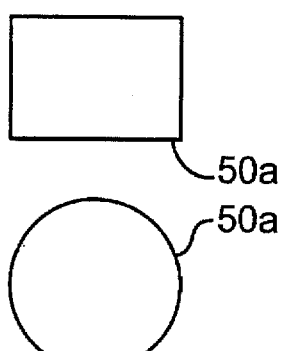
FIG. 2a presents a side view of a PMMA rod used for compression molding.
Figure 2B:
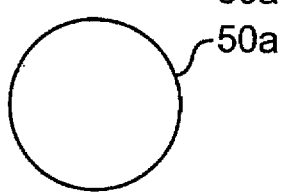
FIG. 2b presents a top view of a PMMA rod used for compression molding.

As a specific example, PMMA is used as the starting material in compression molding in the form of a rod 50a. A typical rod is illustrated in FIG. 2. The rods are first prepared from rod stock. The rod stock is lathed or centerless ground to a diameter ranging between 8 mm and 13 mm, preferably 11 mm, and then cut to a length between 14 mm and 5 mm, preferably 8 mm. The sheet material which has a thickness in the range from $\frac{1}{5}$ of an inch to one inch can also be used to prepare the rods.

Figure 3A:
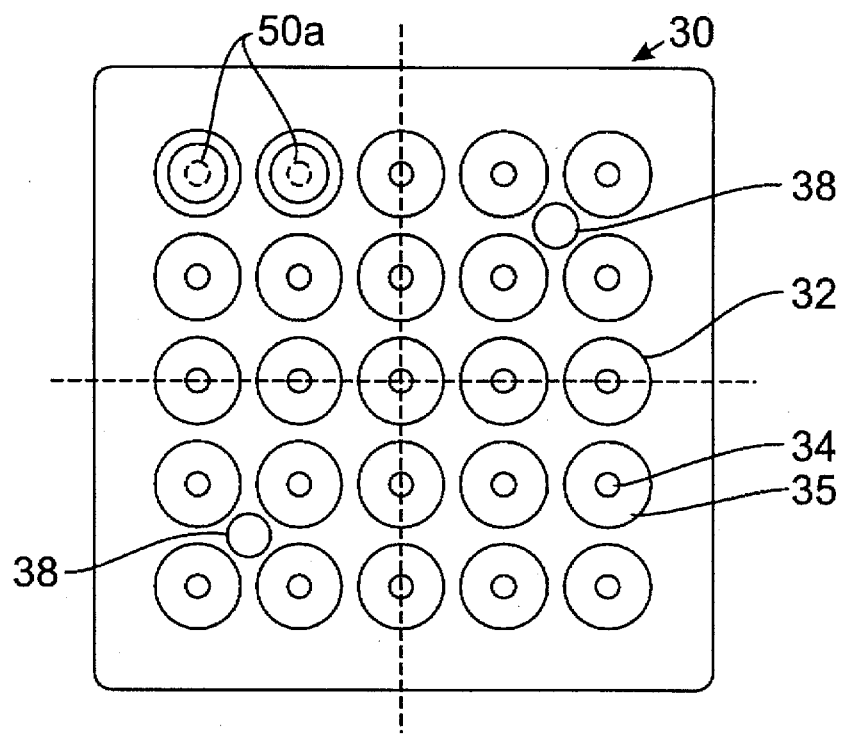
FIG. 3a is a top view of a mold chase used to compression mold the lens blanks.
Figure 3B:
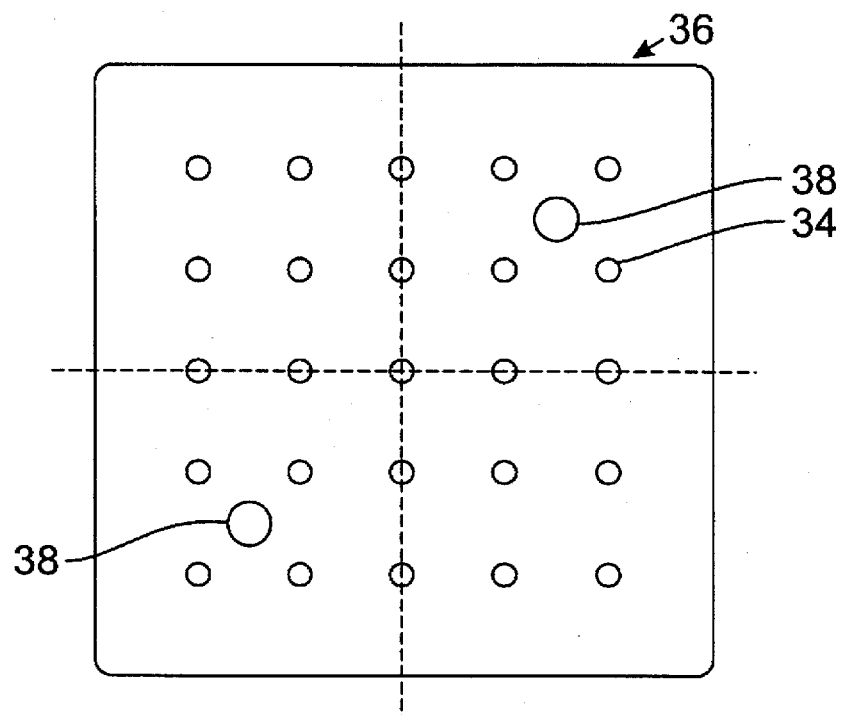
FIG. 3b is a top view of a top plate used to compression mold the lens blanks.
Figure 8:
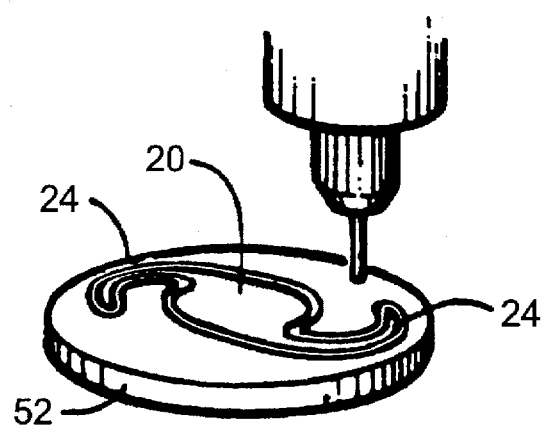
FIG. 8 is a perspective view illustrating the manner in which the one-piece intraocular lens is milled from the molded lens blank made according to the present invention.

The rods are then loaded in a mold chase which is illustrated in FIG. 3a. The mold chase has a mold plate 30 containing a plurality of mushroom-shaped cavities 32. Each cavity 32 consists of a 4 mm diameter by 2.5 mm long stem 34 bearing a 16 mm diameter by 3 mm thick flat cap 35. Each cavity 32 also contains a very shallow recess to hold the rod in place. Referring to FIG. 3b the mold plate 30 is then covered by a top plate 36 consisting an equal number of 4 mm diameter by 2.5 mm long stem cavities 34 via aligning pins 38. The assembled mold chase is placed in a hot press or an oven to uniformly heat the material to a temperature between 120° C. and 210° C., said temperature preferably between 170° C. and 180° C., for 5 to 30 minutes, said time preferably between 15 and 20 minutes. The assembled mold chase is then removed from the hot press or oven to a compression molding machine. A molding pressure in the range of 20,000 lbs to 35,000 lbs is applied to the assembled mold chase. Immediately after the application of pressure, the assembled mold chase is cooled to room temperature under pressure in 1 to 5 minutes by circulating cold water through the mold. It is important that the mold chase is cooled down rapidly to lock in the orientation induced during compression molding.

Figure 4A:
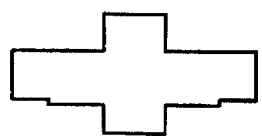
FIG. 4a presents a side view of the resultant lens blanks produced by the invention using a rod configuration in FIG. 2.
Figure 4B:
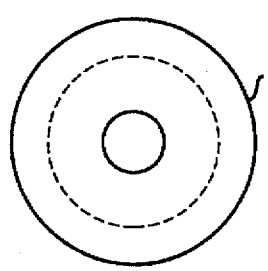
FIG. 4b presents a top view of the resultant lens blank produced by the invention using a rod configuration in FIG. 2.

The molded blanks 50, as illustrated in FIG. 4, are then removed from the mold chase and can then be machined on a lathe to fabricate the one-piece intraocular lenses 20.

Figure 5A:
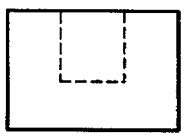
FIG. 5a is a side view of an alternate rod.
Figure 6A:
FIG. 6a is a side view of the resultant lens blank produced by the invention using a rod configuration in FIG. 5.
Figure 5B:
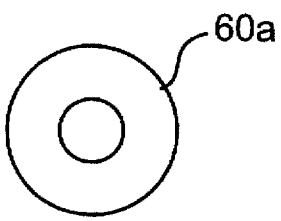
FIG. 5b is a top view of an alternate rod.
Figure 6B:
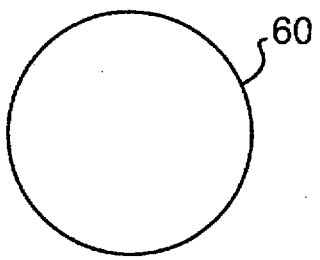
FIG. 6b is a top view of the resultant lens blank produced by the invention using a rod configuration in fig. 5.

An alternate rod 60a configuration can be shaped like a well with the center 4 mm zone removed. The alternate rod and molded blanks 60 can be found in FIGS. 5 and 6, respectively. The thickness of the center 4 mm zone of the rod is identical to the thickness of a molded lens blank. The critical factor regarding the present invention is that little or no compression strain is introduced in the center 4 mm optic zone during compression molding of the molded blank. The compression strain is defined as ratio of a specific dimension, such as thickness, after compression molding to that before molding. This is accomplished by maintaining the thickness or height dimension of the center 4 mm optic zone in the rod before compression molding equal to that in the molded blank after molding.

Figure 7A:
FIG. 7a is a side view of an alternate embodiment of the invention using a composite rod and having a colored portion.
Figure 7B:
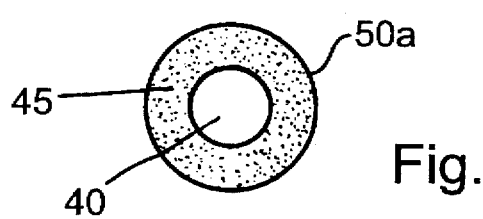
FIG. 7b is a top view of an alternate embodiment of the invention using a composite rod and having a colored portion.

In another embodiment of this invention, the haptics are tinted or colored to provide a better visual aid during surgery by incorporation of a suitable dye or pigment into the haptic composition. One method of making a two color composite lens blank as illustrated in FIG. 7, involves molding a two color composite rod 50a containing a clear optic core 40 and tinted annular region 45. Two-color composite rod stock or sheet stock is made by casting colored methyl methacrylate (MMA) monomer solution or prepolymer over the non-colored optic rod. It is important that the optic zone is concentric within the composite rod. The method described above can be used to make two color lens blanks. The colored haptic lens is then fabricated from the molded composite blank using standard lens manufacturing processes.

BRITTLENESS TEST METHOD

Figure 9:
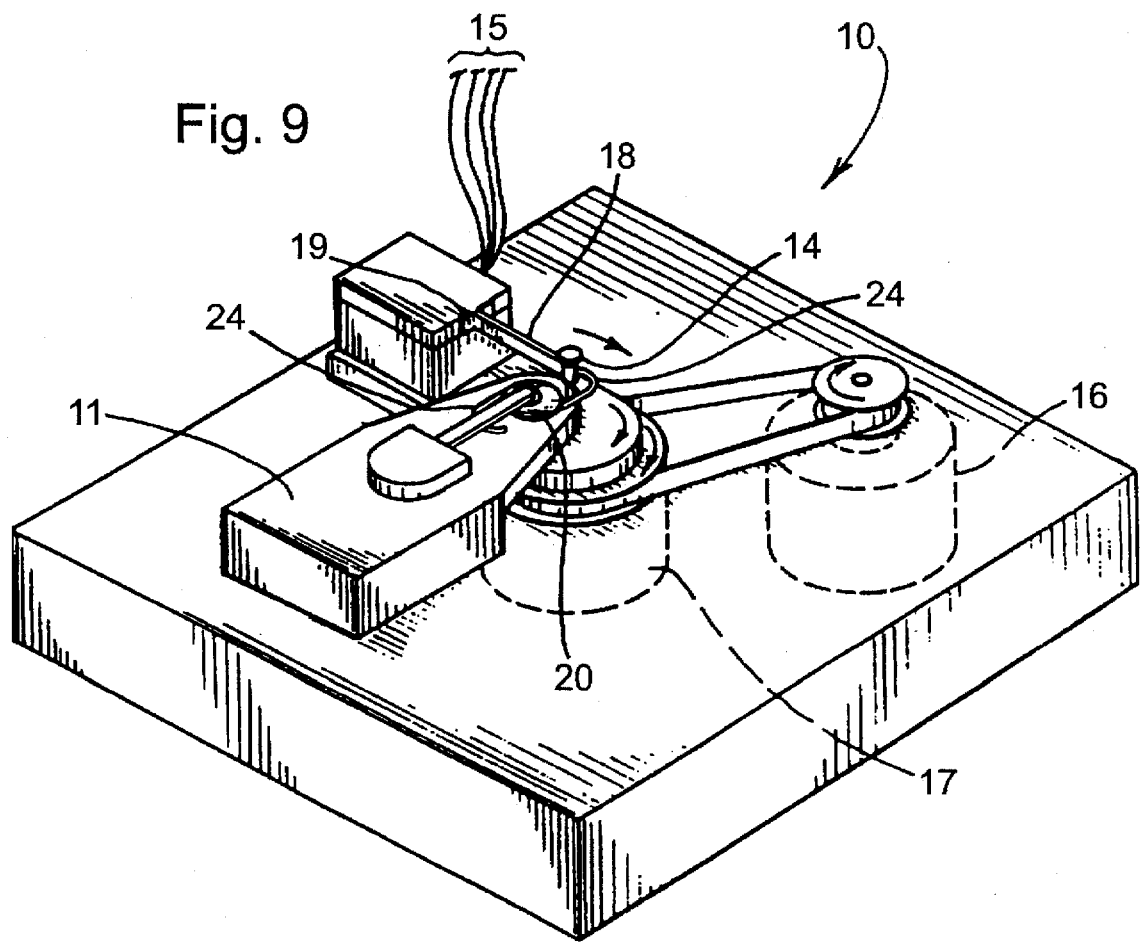
FIG. 9 is a perspective view of a brittleness tester used for determining the resistance to breakage of the haptic of an intraocular lens.

FIG. 9 shows a brittleness tester 10 used for determining the resistance to breakage of the haptic of an intraocular lens. The lens 20 is placed in a fixture 11 that holds the lens securely by the lens body of the lens. As shown more clearly in FIG. 1, the optic-haptic junction of the lens is placed at the center of rotation 13 on the tester. The tester operates by moving the rotatable pin 14 against one of the haptics 24. This forces the haptic to rotate around the center of rotation 13 in a clockwise direction. The speed of rotation can be controlled from a computer interface 15, and can be varied up to 900 degrees per second using stepper motor 16. The maximum rotation angle is 140°. The encoder 17 accurately measures the rotation angle and feeds the information through the computer interface. The rotating arm 18 and strain gauge 19 allow the accurate measurement of force necessary to move the haptic. The individual thickness and width measurements are entered into a computer in order to calculate stress from the force measurements. A stress-angle curve obtained through brittleness testing is similar to a typical stress strain curve obtained by conventional mechanical testing. Stress strain testing gives an indication of the strength of a material and also its toughness. Toughness is defined as the area under the stress-strain curve or stress-angle curve. The brittleness tester is, therefore, an effective tool to evaluate haptic performance against breakage.

EXAMPLE 1

Compression Molded Lens

Lenses were fabricated as shown in FIGS. 2, 3 and 4 from compression molded blanks 50 using rod configuration 50a described above in accordance with the standard lens manufacturing procedures. The brittleness test results of the compression molded lenses and a conventional lens designated as control #1 are presented in Table 1.

TABLE 1

| | | Brittleness Test Results | | |
|---|---|---|---|---|
| Ex. No. | Sample ID | Lens Type | Max. Angle or Angle at Break, deg | Fracture Rate, % |
| Control #1 | Intraocular Lens | UV grade grade PMMA Iolab 8590B | 56 | 100 |
| #1 | Intraocular Lens | UV grade comp. molded PMMA Iolab 8590B | 140 | 0 |

As shown from the data in Table 1, lenses from control #1 show typical haptic fracture characteristics for conventional PMMA lenses. In contrast, the data indicate no haptic breakage upon brittleness testing for the lens of this invention. Thus, the results demonstrate the ductile and flexible nature of the haptics which have been processed through compression molding.

EXAMPLE 2

Compression Molded Colored Haptic Lenses

Colored haptic lenses were fabricated from compression molded blanks 50 using the composite rod configuration 50a described in the present invention in accordance with the standard lens manufacturing procedures. The brittleness test results of the compression molded colored haptic lenses and a conventional lens designated as control #2 are presented in Table 2.

TABLE 2

| | | Brittleness Test Results | | |
|---|---|---|---|---|
| Ex. No. | Sample ID | Lens Type | Max. Angle or Angle at Break, deg | Fracture Rate, % |
| Control #2 | Intraocular Lens | UV grade PMMA with violet haptics Iolab 8591B | 54 | 100 |
| #2 | Intraocular Lens | UV grade comp. molded PMMA with violet haptics Iolab 8591B | 140 | 0 |

As shown from the data in Table 2, lenses from control #2 show typical haptic fracture characteristics for conventional PMMA lenses with violet haptics. In contrast, the data indicate no haptic breakage upon brittleness testing for the lens of this invention. Thus, the results demonstrate the ductile and flexible nature of the haptics which have been processed through compression molding.

BIREFRINGENCE METHOD

Birefringence is one of the simplest methods used for the determination of the orientation in an amorphous, single phase, light transparent polymer, such as PMMA. The technique involves observation of an interference figure using convergent polarized light in a microscope. The birefringence is determined by comparing the colors and interference fringes of the specimen with a color chart. The color chart known as Newton's series is divided into orders by the occurrence of red color that appears regularly as birefringence increases.

EXAMPLE 3
Compression Molded Lenses

Thin discs, approximately 0.25 mm thick, are sectioned horizontally from the lens blank and used to determine the in-plane component of orientation. Vertically sectioned rectangular samples are used to measure the out-of-plane orientation. The birefringence assessments of compression molded blanks made by a prior process are designated as control #3. The results are summarized in Table 3.

TABLE 3

Birefringence Assessments

| Ex. No. | Sample ID | In-Plane Birefringence | Out-of-plane Birefringence |
|---|---|---|---|
| Control #3 | Molded blank from a prior art practiced at IOLAB using IOLAB UV grade PMMA | Isotropic (zero birefringence) in the center 4–9 mm optic zone, first order white color in the periphery outside the central isotropic zone | first order white color |
| #3 | Molded blank from this invention using IOLAB UV grade PMMA | first order white color for entire blank radially oriented | first order white color |

The molded blanks from the previous practice as presented in control #3 show isotropic in-plane orientation and first order white out-of-plane orientation in the center optic zone where the lens optic is located. The preferential orientation in the out-of-plane direction gives rise to enhanced mechanical properties along the thickness dimension of the lens optic and much weaker properties along the plane of the lens. This results in retardation of crack propagation due to YAG laser irradiation through the thickness dimension and therefore demonstrates more extensive lateral cracking. The periphery where the haptics are located shows biaxial orientation in both in-plane and out-plane dimensions. This results in haptics with enhanced mechanical properties and resistance to breakage. The flexibility and resistance to breakage of lenses with compression molded haptics is known from previous lenses in which the entire lens was compression molded—albeit with the disadvantage of undesirable optical characteristics after YAG laser irradiation.

The molded blanks from this invention demonstrate a balanced or equal in-plane and out-of-plane orientation in the lens optic. The balanced orientation implies that equal mechanical strength can be expected in all three dimensions leading to three dimensional cracks as typically observed in the non-oriented lenses upon YAG laser exposure. Furthermore, the blank is biaxially oriented. The orientation in the plane of the blank is radial. The biaxial orientation results in haptic with enhanced mechanical properties and resistance to breakage. This invention represents a great improvement over the prior art compression molded lenses with regard to YAG laser interactions and demonstrates comparable enhanced haptic mechanical property performance against breakage as the prior art molded lenses.

It is understood that by the term "balanced orientation between the planar dimension and the thickness dimension" it is meant that the molecules of the polymer are substantially equally oriented in either dimension to achieve the above property under YAG irradiation. It would be equivalent to have "non-oriented" or unaligned polymer molecules such as by no treatment, leaving the polymer molecules in a random orientation.

The use of the material processed as described herein, provides the haptics of these lenses with markedly improved mechanical property performance. The preceding examples are designed to illustrate the preferred embodiments of this invention, and should not be construed in any way to limit the full breadth and scope of that which is defined as the invention in the appended claims.

We claim:

1. A one-piece intraocular lens having a central optic portion body and at least one filamentary haptic attached to and extending outwardly from the periphery of said optic portion of said lens, the material of said haptic being substantially oriented and the material of the optic region being of substantially balanced orientation on a molecular basis.

2. The lens of claim 1 wherein the material of said haptic has an in-plane direction and an out-of-plane direction and is biaxially oriented.

3. The lens of claim 1 wherein said lens is selected from the group consisting of polymethyl methacrylate and copolymers thereof.

4. The lens of claim 1 wherein said optic region which is of substantially balances orientation has a diameter of at least 4 millimeters.

5. The lens of claim 2 wherein said material of said haptic defines a thickness and is compression molded to provide about 1.2 to about 2.0 compression strain along the direction extending outwardly from the periphery of said optic portion of said lens in combination with about 1.7 to about 4.7 compression strain along the thickness dimension to induce balanced orientation in the optic and highly oriented polymer chains in the haptic.

6. The lens of claim 1 wherein said haptics are colored, and wherein at least an inner portion of said optic portion is colorless and transparent.

7. The lens of claim 2 wherein the in-plane orientation of said biaxial orientation is radial.

8. The lens of claim 1 wherein the material of the optic region has balanced orientation in the in-plane and out-of-plane directions.

9. A one-piece intraocular lens having a central optic portion body and at least one filamentary haptic attached to and extending outwardly from the periphery of said optic portion of said lens, the material of said haptic, which defines a thickness, being substantially oriented and the material of the optic region being of substantially balanced orientation, wherein the material of said haptic is compression molded to provide about 1.2 to about 2.0 compression strain along the direction extending outwardly from the periphery of said optic portion of said lens in combination with about 1.7 to about 4.7 compression strain along the thickness dimension to induce balanced orientation in the optic and highly oriented polymer chains in the haptic.

* * * * *